(12) United States Patent
Kim et al.

(10) Patent No.: US 12,122,812 B2
(45) Date of Patent: Oct. 22, 2024

(54) METHOD FOR PREPARING BIOMATERIAL HAVING SELECTIVELY FUNCTIONALIZED TYROSINE, BIOMATERIAL HAVING SELECTIVELY FUNCTIONALIZED TYROSINE, AND PHARMACEUTICAL COMPOSITION CONTAINING SAME AS ACTIVE INGREDIENT

(71) Applicant: SEOUL NATIONAL UNIVERSITY R&DB FOUNDATION, Seoul (KR)

(72) Inventors: Byeong Moon Kim, Seoul (KR); Yan Lee, Seoul (KR); Eun Joung Choi, Seoul (KR); Dongwook Jung, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 803 days.

(21) Appl. No.: 16/979,078

(22) PCT Filed: Mar. 5, 2019

(86) PCT No.: PCT/KR2019/002512
§ 371 (c)(1),
(2) Date: Sep. 8, 2020

(87) PCT Pub. No.: WO2019/172605
PCT Pub. Date: Sep. 12, 2019

(65) Prior Publication Data
US 2021/0054038 A1    Feb. 25, 2021

(30) Foreign Application Priority Data
Mar. 6, 2018 (KR) .................. 10-2018-0026582

(51) Int. Cl.
| | |
|---|---|
| C07K 1/13 | (2006.01) |
| A61K 47/60 | (2017.01) |
| C07K 14/505 | (2006.01) |
| C07K 19/00 | (2006.01) |
| A61K 38/00 | (2006.01) |

(52) U.S. Cl.
CPC ............ C07K 14/505 (2013.01); A61K 47/60 (2017.08); C07K 19/00 (2013.01); C12Y 304/21001 (2013.01); A61K 38/00 (2013.01)

(58) Field of Classification Search
None
See application file for complete search history.

(56) References Cited

U.S. PATENT DOCUMENTS

| | | | |
|---|---|---|---|
| 2009/0252703 A1* | 10/2009 | Gegg, Jr. ........... | C07K 1/1077 424/85.2 |
| 2015/0315340 A1* | 11/2015 | Dong ................ | C08G 64/06 528/21 |

FOREIGN PATENT DOCUMENTS

| | | |
|---|---|---|
| KR | 10-2017-0104535 | 9/2017 |
| WO | WO 2015/188120 A1 | 12/2015 |

OTHER PUBLICATIONS

Dozier, J. K., et al. Int. J. Mol. Sci. (2015), 16; 25831-25864.*
Dong, J., et al. Angew. Chem. (2014), 53, 9430-9448.*
Jones, M. W., et al. JACS (2012), 134(7); 7406-7413.*
Cheetham, Janet C. et al.; "NMR structure of human erythropoietin and a comparison with its receptor bound conformation." Nat. Struct. Biol. (1996) 5(10) 181-186).*
Chen et al., "Arylfluorosulfates Inactivate Intracellular Lipid Binding Protein(s) Through Chemoselective SuFEx Reaction with a Binding-Site Tyr Residue," J Am Chem Soc. 138.23: 7353-7364, Jun. 2016.
International Search Report from parent PCT Application No. PCT/KR2019/002512, 7 pages (mailed May 31, 2019), w/English Translation.
Choi et al., "Chemoselective Tyrosine Bioconjugation through Sulfate Click Reaction," Chemistry 24.43: 10948-10952, Aug. 2018.
Fadeyi et al., "Covalent Enzyme Inhibition through Fluorosulfate Modification of a Non-Catalytic Serine Residue," ACS Chem Biol. 12.8: 2015-2020, Jul. 2017.
Li et al., "Direct introduction of R-SO2F moieties into proteins and protein-polymer conjugation using SuFEx chemistry," Polymer 99: 7-12, Jun. 2016.
Wang et al., "PEGylation markedly enhances the in vivo potency of recombinant human non-glycosylated erythropoietin: A comparison with glycosylated erythropoietin," J Control Release 145.3: 306-313, Aug. 2010.

* cited by examiner

*Primary Examiner* — Fred H Reynolds
(74) *Attorney, Agent, or Firm* — Klarquist Sparkman, LLP

(57) ABSTRACT

Disclosed are a method for preparing a biomaterial having selectively functionalized tyrosine, a biomaterial having selectively functionalized tyrosine, and a pharmaceutical composition containing same as an active ingredient. The method for preparing a biomaterial to which a compound represented by chemical formula 2 is coupled, of the present invention, allows the compound represented by chemical formula 2 to be selectively coupled, in a high yield in a biomaterial, to tyrosine, which is present on the surface of an aqueous solution such that the coupling thereof to amino acids other than tyrosine does not occur and, when only one tyrosine is present, heterogeneous mixtures are not present and the inherent activity of the biomaterial is maintained, and thus the compound can be effectively used as a pharmaceutical composition containing a biomaterial drug as an active ingredient. In addition, the method can selectively functionalize tyrosine, and thus can be effectively used for tyrosine functionalization in a biomaterial.

20 Claims, 6 Drawing Sheets

[fig 1]
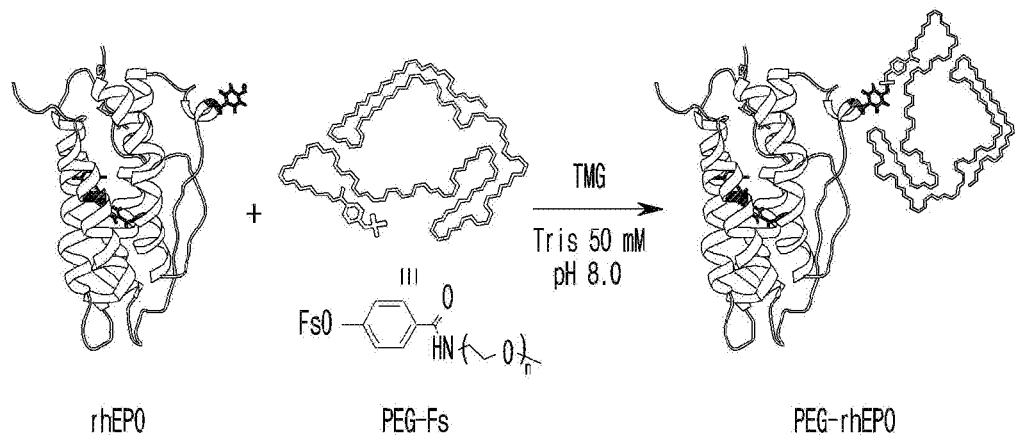
[fig 2]
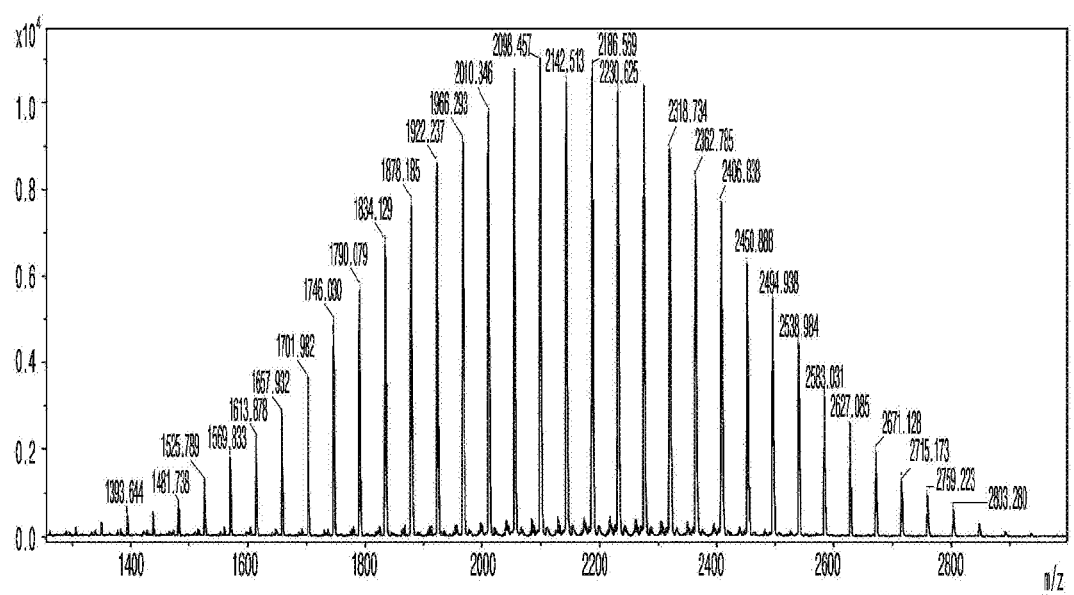

[fig 3]
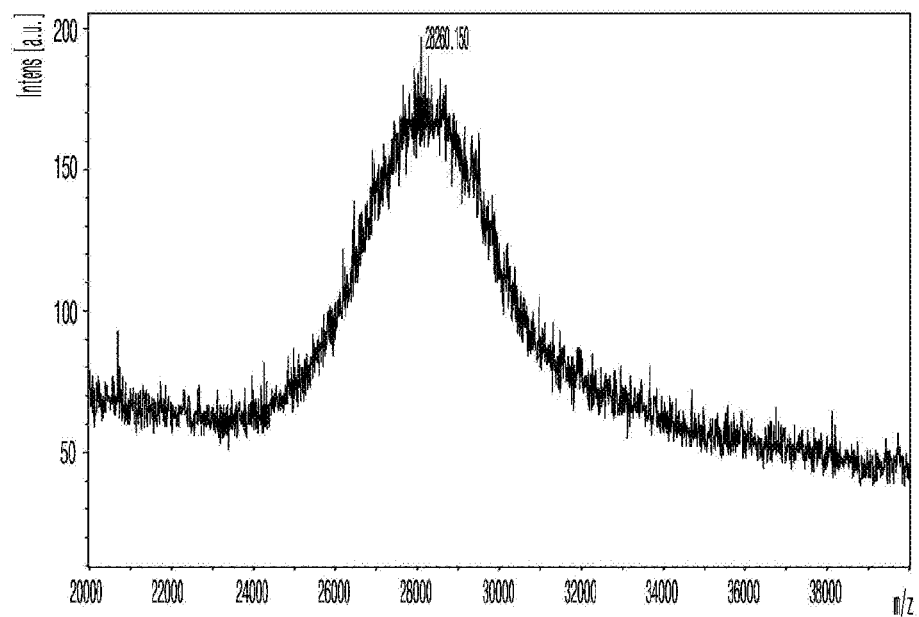
[fig 4]
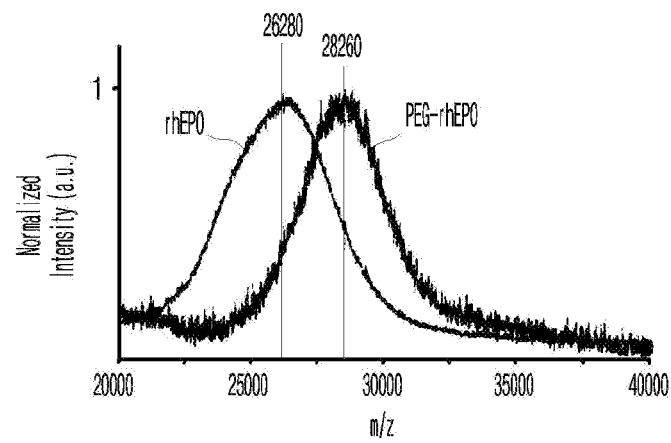

[fig 5a]
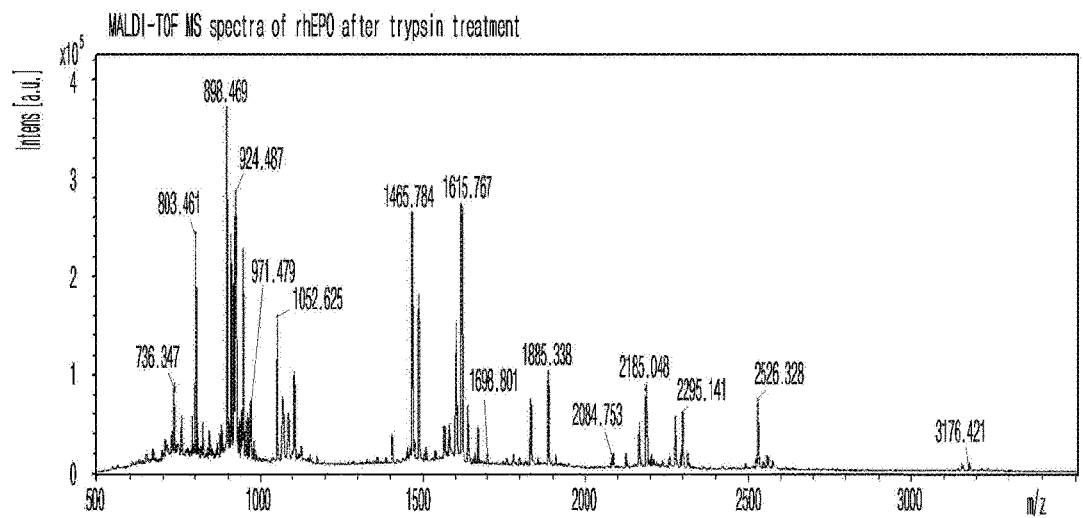
[fig 5b]
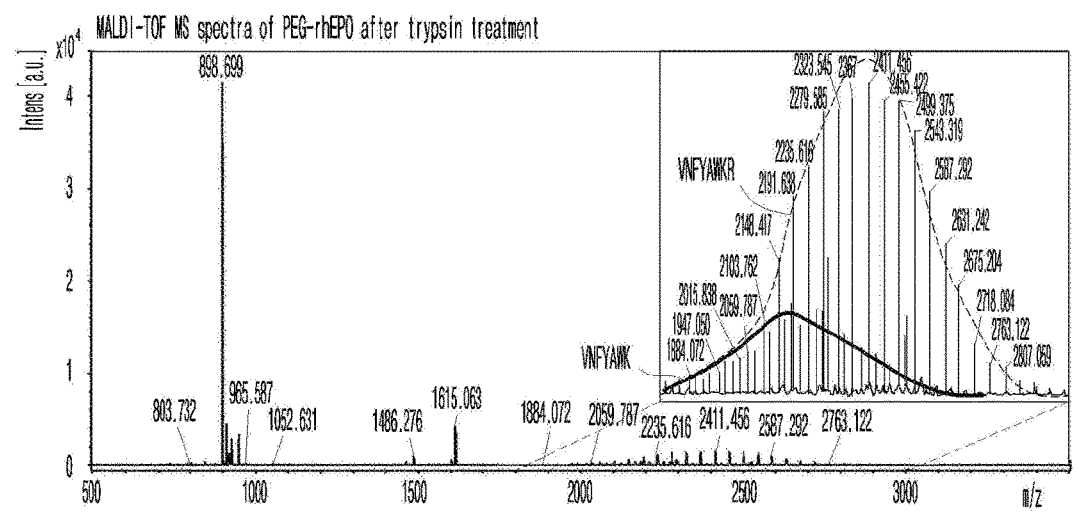

[fig 6]
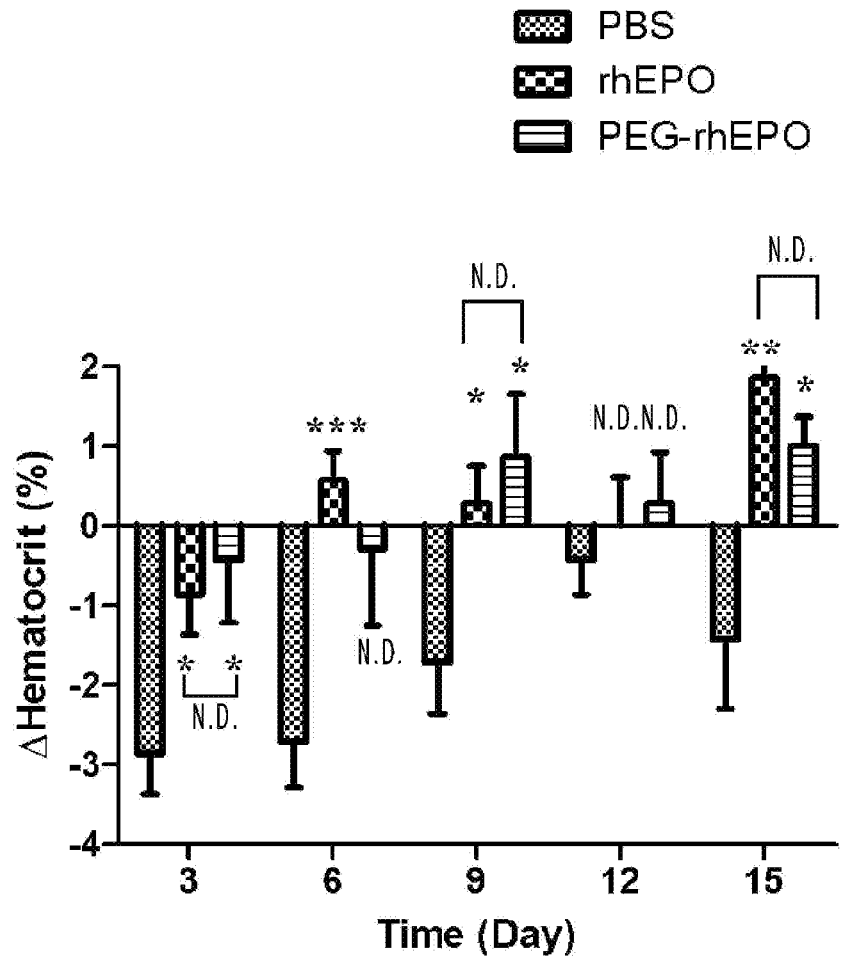
[fig 7a]
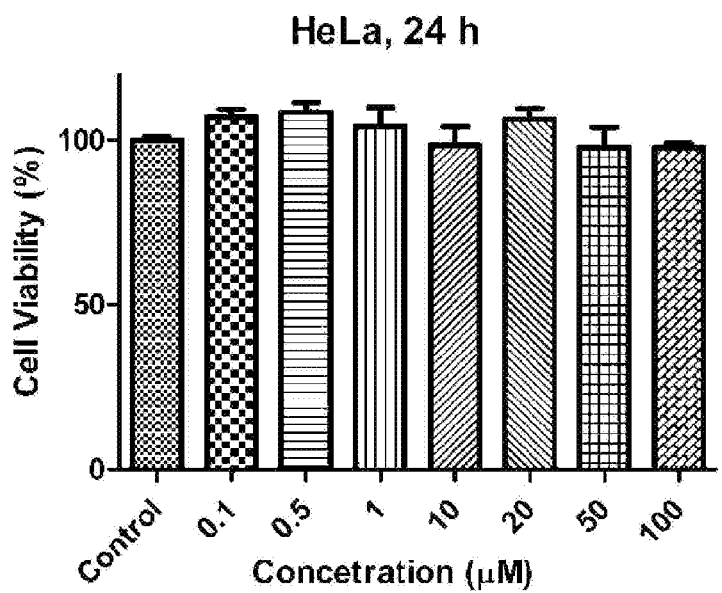

[fig 7b]
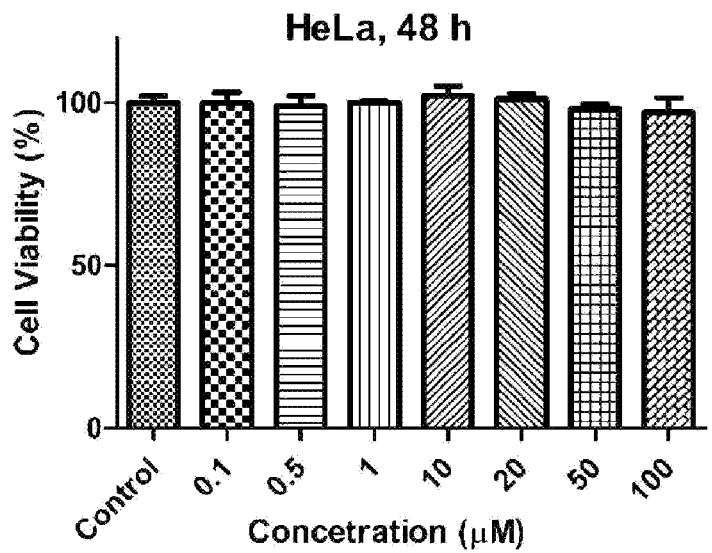
[fig 8]
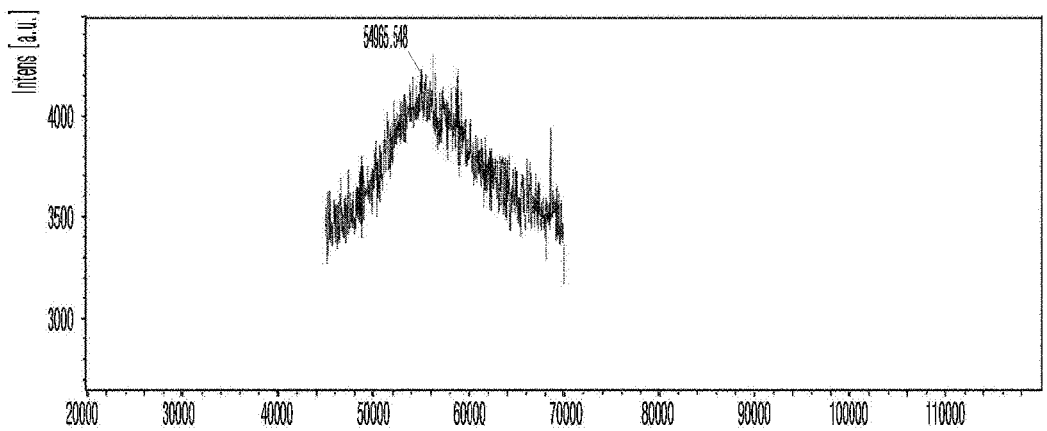

【fig 9a】
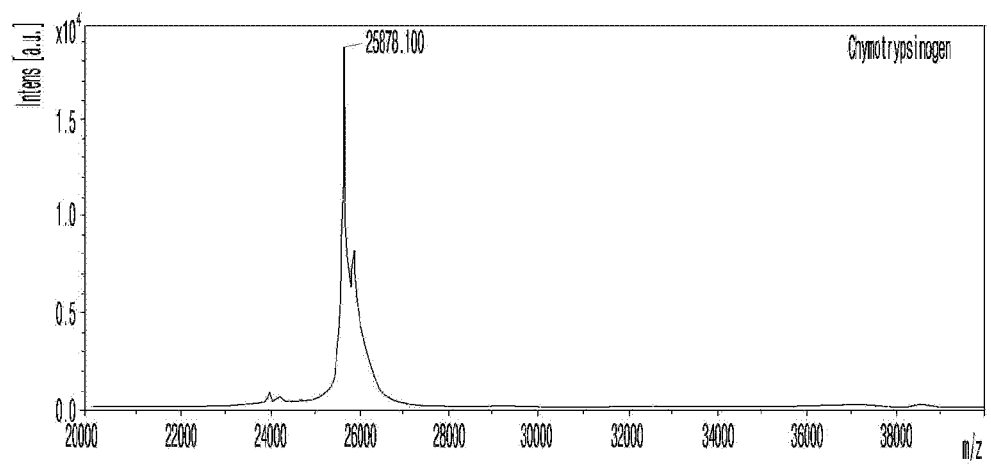
【fig 9b】
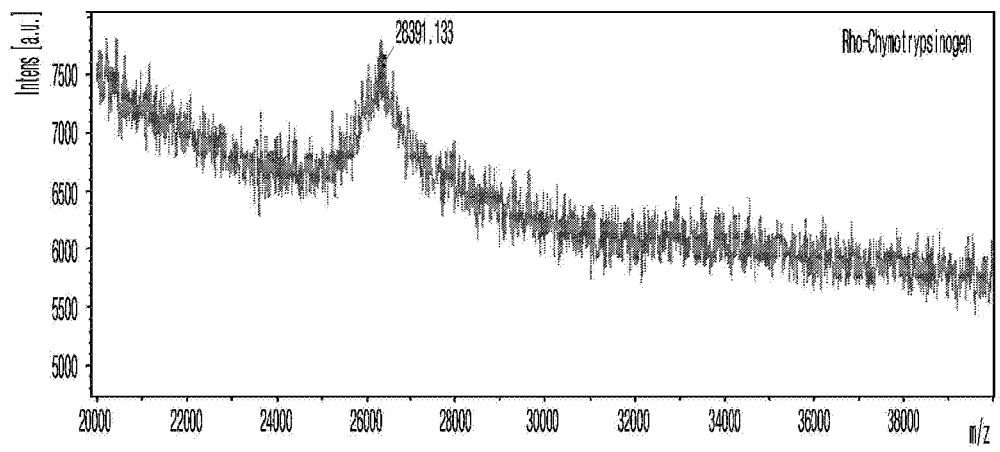

METHOD FOR PREPARING BIOMATERIAL HAVING SELECTIVELY FUNCTIONALIZED TYROSINE, BIOMATERIAL HAVING SELECTIVELY FUNCTIONALIZED TYROSINE, AND PHARMACEUTICAL COMPOSITION CONTAINING SAME AS ACTIVE INGREDIENT

CROSS REFERENCE TO RELATED APPLICATIONS

This is the U.S. National Stage of International Application No. PCT/KR2019/002512, filed Mar. 5, 2019, which in turn claims priority of Korean Patent Application No. 10-2018-0026582, filed Mar. 6, 2018, which application is incorporated herein in its entirety.

TECHNICAL FIELD

The present invention relates to a method for preparing a biomaterial having selectively functionalized tyrosine and a pharmaceutical composition containing the same as an active ingredient.

BACKGROUND ART

In order to control the biological system, it is important to control the functions of proteins, in particular, the functions of proteins related to signaling pathways. Among the numerous approaches to control protein function, protein- or peptide-based drugs (PBDs) are attracting attention because they can effectively regulate protein-protein interactions due to their structural properties that they can be covered by drugs with a large contact area but low molecular weight at the site of action of protein-protein interactions (PPI).

However, although the protein- or peptide-based drugs (PBDs) have excellent target specificity and efficacy, they have a disadvantage in that the application is limited due to the low stability and short duration in physiological environments.

Thus, in order to improve the pharmacokinetic profiles, artificial functionalization such as incorporating unnatural amino acids (UAA) for conjugation of PBD with polymers or the like or for conjugation with other useful tethers is being tried. In such artificial functionalization, it is important to maintain the intrinsic activity of the protein.

However, when proteins are non-selectively functionalized, heterogeneous mixtures with a sharp decrease in activity may be produced, or in the worst case, the entire protein function may be lost. Therefore, it is important to functionalize a specific site without altering the site important to the function of the protein (target binding site) or the allosteric site.

Unlike pure biological reactions such as enzyme reactions, most biochemical reactions that functionalize proteins can be classified into the following two types: 1) functionalizing a genetically altered non-natural amino acid residue (UAA residue) in a protein, or 2) functionalizing a specific natural amino acid residue of a native protein selectively through a chemical reaction.

As a method of functionalizing the non-natural amino acid, there is a method of conjugating azidophenylalanine to a protein backbone. However, the method of conjugating such a non-natural amino acid has a problem that it is complicated and the amount of expression is very low.

On the other hand, there are many examples of methods of functionalizing the natural amino acid. For example, lysine (Lys)-succinamide and cysteine (Cys)-maleimide coupling reactions are widely used for functionalization of natural amino acids. In the lysine (Lys)-succinamide coupling reaction, most proteins have a large number of lysines on the surface, and thus non-selective reactions occur, resulting in the production of a mixture. In the cysteine (Cys)-maleimide coupling reaction, functionalization may occur when there is cysteine on the protein surface. However, most proteins do not have cysteine residues on the surface, and even if they have cysteine residues, they are easily oxidized to become disulfide groups. Moreover, since lysine participates in the reaction with maleimide under normal conditions, it is very difficult to find a condition in which only cysteine residues are selectively reacted. Therefore, there is a need to develop a novel method capable of selectively and efficiently functionalizing specific natural amino acid residues.

Meanwhile, EPO (erythropoietin) is a glycoprotein hormone that induces erythrocyte production, and rhEPO (recombinant human erythropoietin) is one of the most marketable protein drugs in the global drug market as a therapeutic agent for severe anemia caused by chronic kidney disease (CKD). As a means to improve the pharmacokinetic stability of rhEPO and reduce the number of drug administrations, rhEPO linked with polyethylene glycol (PEG) is widely used as a second generation drug. (Patent Reference 1) Korean Patent Publication No. 10-2017-0104535.

PEG conjugation, that is PEGylation, forms a hydrated polymeric layer that reduces immunogenicity, renal clearance and enzymatic degradation of the protein around the protein. Mircera, a PEGylated form of the rhEPO drug, exhibits a remarkably prolonged pharmacokinetic half-life and is administered much less frequently than the unmodified drug. However, the PEGylation of Mircera is based on Lys-succinimide chemistry, and it mostly reacts with Lys-45 or Lys-52 of the 7 lysine residues on the rhEPO surface, resulting in the production of a heterogeneous mixture of PEGylated rhEPO isomers, which makes purification difficult.

Technical Problem

It is an object of the present invention to provide a method for preparing a biomaterial in which a specific compound is bound to the biomaterial containing tyrosine present on the surface in an aqueous solution.

It is another object of the present invention to provide a protein in which a specific compound is bound to the biomaterial containing tyrosine present on the surface in an aqueous solution.

It is another object of the present invention to provide a method for PEGylating a biomaterial containing tyrosine present on the surface in an aqueous solution.

It is another object of the present invention to provide a composition for hematopoiesis.

Technical Solution

To achieve the above objects, in one aspect of the present invention, the present invention provides a method for preparing a biomaterial to which a compound represented by formula 2 is coupled comprising a step of reacting a compound represented by formula 1 and a biomaterial containing tyrosine present on the surface in an aqueous solution in the presence of a compound represented by formula 3:

[Formula 1]

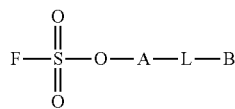

(In formula 1,

A is nonsubstituted or substituted $C_{6-14}$ arylene or 5-20 membered nonsubstituted or substituted heteroarylene, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, $R^3$ is hydrogen or straight or branched $C_{1-3}$ alkyl; and B is a compound for imparting functionality to a biomaterial);

[Formula 2]

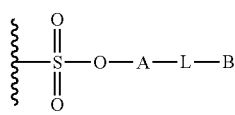

(In formula 2,
A, L and B are as defined in formula 1);

[Formula 3]

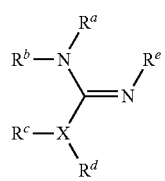

(In formula 3,
X is N or CH; and
$R^a$, $R^b$, $R^c$, $R^d$ and $R^e$ are independently hydrogen or straight or branched $C_{1-5}$ alkyl, $R^a$ and $R^e$ can form 5-8 membered heterocycloalkenyl along with N to which they are attached, and $R^b$ and $R^C$ can form 5-8 membered heterocycloalkyl along with N and X to which they are attached).

In another aspect of the present invention, the present invention provides a protein in which a compound represented by formula 2 is bound to —OH group of tyrosine of the biomaterial containing tyrosine present on the surface in an aqueous solution:

[Formula 2]

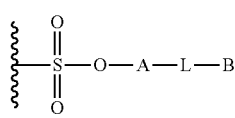

(In formula 2,
A, L and B are as defined in formula 1 in a method for preparing a biomaterial to which a compound represented by formula 2 is coupled).

In another aspect of the present invention, the present invention provides a method for PEGylating a biomaterial comprising a step of reacting a compound represented by formula 1 and a biomaterial containing tyrosine present on the surface in an aqueous solution in the presence of a compound represented by formula 3:

[Formula 1]

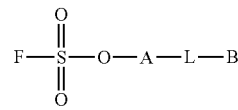

(In formula 1,

A is nonsubstituted or substituted $C_{6-14}$ arylene or 5-20 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, $R^3$ is hydrogen or straight or branched $C_{1-3}$ alkyl; and B is alkoxy or hydroxy polyalkyleneoxide having a weight average molecular weight of 100 to 50000, wherein alkoxy is straight or branched $C_{1-10}$ alkoxy, and alkylene is straight or branched $C_{1-10}$ alkylene);

[Formula 3]

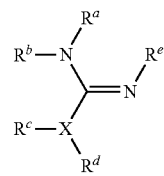

(In formula 3,
X is N or CH; and
$R^a$, $R^b$, $R^c$, $R^d$ and $R^e$ are independently hydrogen or straight or branched $C_{1-5}$ alkyl, $R^a$ and $R^e$ can form 5-8 membered heterocycloalkenyl along with N to which they are attached, and $R^b$ and $R^C$ can form 5-8 membered heterocycloalkyl along with N and X to which they are attached).

In another aspect of the present invention, the present invention provides a composition for hematopoiesis comprising EPO (erythropoietin), a biomaterial containing tyrosine present on the surface in an aqueous solution, to which a compound represented by formula 2 is bound to —OH group of the tyrosine as an active ingredient:

[Formula 2]

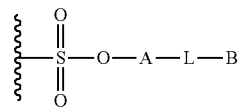

(In formula 2,
A, L and B are as defined in formula 1 of claim 1).

Advantageous Effects

The method for preparing a biomaterial to which a compound represented by formula 2 is coupled, of the present invention, allows the compound represented by formula 2 to be selectively coupled, in a high yield in a biomaterial, to tyrosine, which is present on the surface in an aqueous solution such that the coupling thereof to amino acids other than tyrosine does not occur and, when only one tyrosine is present, heterogeneous mixtures are not present and the inherent activity of the biomaterial is maintained, and thus the compound can be effectively used as a pharmaceutical composition containing a biomaterial drug as an active ingredient. In addition, the method can selectively functionalize tyrosine, and thus can be effectively used for tyrosine functionalization in a biomaterial.

DESCRIPTION OF DRAWINGS

FIG. 1 is a schematic diagram showing the reaction of Example 1.

FIG. 2 is a graph showing the MALDI-TOF MS measurement results of the compound of Preparative Example 3.

FIG. 3 is a graph showing the MALDI-TOF MS measurement results of PEG-rhEPO of Example 1.

FIG. 4 is a graph showing the comparison of the MALDI-TOF MS measurement results of rhEPO before PEGylation and rhEPO after PEGylation (PEG-rhEPO) of Example 1.

FIGS. 5a-5b are diagrams showing the results of performing trypsin digestion evaluation with the non-PEGylated rhEPO of Experimental Example 3 (MALDI-TOF spectrum) (FIG. 5a), and the result of performing trypsin digestion evaluation with the PEGylated rhEPO prepared in Example 1 (MALDI-TOF spectrum) (FIG. 5b).

FIG. 6 is a graph showing the hematopoietic function of PEG-rhEPO of Experimental Example 4.

FIGS. 7a-7b are a set of graphs showing the cytotoxicity test results of the aryl compound containing sulfate of Experimental Example 5. FIG. 7a: 24 hour cultivation, FIG. 7b: 48 hour cultivation.

FIG. 8 is a graph showing the MALDI-TOF MS measurement results of PEG-rhEPO of Example 2.

FIGS. 9a-9b are a set of graphs showing the MALDI-TOF MS measurement results of chymotrypsinogen without rhodamine (FIG. 9a) and the MALDI-TOF MS measurement results of chymotrypsinogen with rhodamine of Example 3 (FIG. 9b).

BEST MODE

Hereinafter, the present invention is described in detail.

In one aspect of the present invention, the present invention provides a method for preparing a biomaterial to which a compound represented by formula 2 is coupled comprising a step of reacting a compound represented by formula 1 and a biomaterial containing tyrosine present on the surface in an aqueous solution in the presence of a compound represented by formula 3.

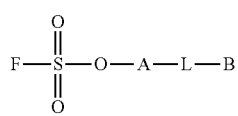

[Formula 1]

(In formula 1,

A is nonsubstituted or substituted $C_{6-14}$ arylene or 5-20 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, $R^3$ is hydrogen or straight or branched $C_{1-3}$ alkyl; and B is a compound for imparting functionality to a biomaterial);

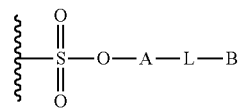

[Formula 2]

(In formula 2,

A, L and B are as defined in formula 1);

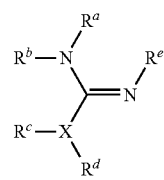

[Formula 3]

(In formula 3,

X is N or CH; and $R^a$, $R^b$, $R^c$, $R^d$ and $R^e$ are independently hydrogen or straight or branched $C_{1-5}$ alkyl, $R^a$ and $R^e$ can form 5-8 membered heterocycloalkenyl along with N to which they are attached, and $R^b$ and $R^c$ can form 5-8 membered heterocycloalkyl along with N and X to which they are attached).

A is nonsubstituted or substituted $C_{6-10}$ arylene or 5-15 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-3}$ alkyl, straight or branched $C_{1-3}$ alkoxy, =O and —OH.

A can be phenylene, xanthine or coumarin.

In the preparation method of the present invention, —OH of tyrosine and —F of the compound represented by formula 1 react in the presence of the compound in an aqueous solution. At this time, the structure of A does not affect the reaction, and is not limited to a specific structure.

B is a compound for imparting functionality to a biomaterial. The compound may mean a biocompatible polymer. In addition, the compound for imparting functionality to the biomaterial can be an organic or inorganic fluorescent substance. The organic fluorescent substance can be rhodamine. To impart functionality to the biomaterial means to impart specific functionality to the biomaterial (functionalization), such as functionalization of the biomaterial itself (e.g., PEGylation), attachment of antibodies or complements, and attachment of fluorescent substances, and B can be used without restrictions as long as it makes this possible.

As an example, B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly (alkyl methacylate) having a weight average molecular weight of 100 to 50000, and peptide polymers having a weight average molecular weight of 100 to 50000, wherein alkoxy can be straight or branched $C_{1-10}$ alkoxy, alkylene can be straight or branched $C_{1-10}$ alkylene, and alkyl can be straight or branched $C_{1-10}$ alkyl.

B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly(alkyl methacylate) having a weight average molecular weight of 100 to 50000, and peptide polymers having a weight average molecular weight of 100 to 50000, wherein alkoxy can be straight or branched $C_{1-5}$ alkoxy, alkylene can be straight or branched $C_{1-5}$ alkylene, and alkyl can be straight or branched $C_{1-5}$ alkyl.

B is alkoxy or hydroxypolyalkyleneoxide having a weight average molecular weight of 100 to 50000, wherein alkoxy can be straight or branched $C_{1-3}$ alkoxy, and alkylene can be straight or branched $C_{1-3}$ alkylene.

B can be methoxy polyethyleneoxide having a weight average molecular weight of 100 to 50000.

In the B, the peptide polymer can be a polymer randomly bound with one or more amino acids selected from the natural amino acid group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine and tryptophan.

The weight average molecular weight of B can be 100 to 50000.

The weight average molecular weight of B can be 500 to 40000.

The weight average molecular weight of B can be 1000 to 30000.

At this time, the weight average molecular weight may vary depending on the weight average molecular weight of the B starting material used in the preparation of the compound represented by formula 1.

In the preparation method of the present invention, —OH of tyrosine and —F of the compound represented by formula 1 react in the presence of the compound in an aqueous solution. At this time, the structure of B does not affect the reaction, and is not limited to a specific structure.

L can be any one selected from the group consisting of S, O, $NR^3$, —NHC(=O)—, —C(=O)NH— and straight or branched $C_{1-5}$ alkylene, or a combination thereof, and $R^3$ can be hydrogen or straight or branched $C_{1-3}$ alkyl.

L can be any one selected from the group consisting of —NHC(=O)—, —C(=O)NH— and straight or branched $C_{1-5}$ alkylene, or a combination thereof.

In the preparation method of the present invention, —OH of tyrosine and —F of the compound represented by formula 1 react in the presence of the compound in an aqueous solution. At this time, the structure of L does not affect the reaction, and is not limited to a specific structure.

In the compound represented by formula 3, when X is N, the compound represented by formula 3 may be a guanidine derivative. In addition, $R^b$, $R^c$, $R^d$ and $R^e$ are independently hydrogen or straight or branched $C_{1-3}$ alkyl. Further, $R^a$, $R^b$, $R^c$, $R^d$ and $R^e$ are independently hydrogen or methyl.

When X is CH, the compound represented by formula 3 may be an amidine derivative.

$R^a$, $R^b$, $R^c$, $R^d$ and $R^e$ are independently hydrogen or straight or branched $C_{1-3}$ alkyl, $R^a$ and $R^e$ can form 6 membered heterocycloalkenyl along with N to which they are attached, and $R^b$ and $R^c$ can form 7 membered heterocycloalkyl along with N and X(CH) to which they are attached.

$R^a$, $R^b$, $R^c$, $R^d$ and $R^e$ are independently hydrogen or methyl.

The compound represented by formula 3 can be DBU (1,8-Diazabicyclo(5.4.0)undec-7-ene) or TMG (1,1,3,3-tetramethylguanidine).

The compound represented by formula 3 can be TMG (1,1,3,3-tetramethylguanidine).

The preparation method of the present invention is characterized in that —OH of tyrosine and —F of the compound represented by formula 1 react in the presence of a compound represented by formula 3 in an aqueous solution. In order for the reaction to proceed in an aqueous solution, a compound represented by formula 3 is required. When the reaction proceeds with an amine other than the compound represented by formula 3, the reaction may not proceed, or a problem may arise that the selectivity for tyrosine is lowered (see Experimental Example 1 and Table 1).

Considering that the environment in which the biomaterial is present is in an aqueous solution, the compound represented by formula 3 can preferably be a compound having a structure showing hydrophilicity, and more preferably TMG (see Experimental Example 1 and Table 1).

In the biomaterial containing tyrosine present on the surface in an aqueous solution of the preparation method, the tyrosine can be present in the hydrophilic region.

The biomaterial is not limited as long as it is a biomaterial containing tyrosine present on the surface in an aqueous solution, but can be any one selected from the group consisting of proteins selected from the group consisting of peptides, peptidomimetics, antibodies, enzymes, peptide-based hormones and complements; antibody-drug conjugates; and protein-polymer conjugates.

The biomaterial can be EPO (erythropoietin), chymotrypsinogen A, or activated chymotrypsin.

In the preparation method, a polar solvent selected from the group consisting of $C_{1-5}$ lower alcohols and DMSO (dimethyl sulfoxide) can be further added to react.

The polar solvent can be used for increasing the solubility of the compound represented by formula 1 when the biomaterial is reacted with the compound represented by formula 1.

According to an embodiment of the present invention, when rhEPO (recombinant human EPO (erythropoietin)) is used as a characteristic biomaterial of the present invention, the compound represented by formula 2 selectively binds only to the outer surface of rhEPO, that is, Tyr-49 present in an aqueous solution. In addition, none of the internal tyrosine residues bind to the compound (see Experimental Example 3 and Tables 3 and 4).

In addition, according to an embodiment of the present invention, when rhEPO (recombinant human EPO (erythropoietin)) is used as a biomaterial, the compound represented by formula 2 selectively binds only to Tyr-49 present in an aqueous solution, and thus which maintains the hematopoietic function, an inherent function of EPO (see Experimental Example 4 and FIG. 6).

According to the preparation method of the present invention, the binding reaction with other amino acids or tyrosine in the inside of a biomaterial (for example, the inside of a protein, the part that is not in contact with the aqueous solution) does not occur in an aqueous solution that is not present on the surface in the aqueous solution by selectively binding the compound represented by formula 2 to the tyrosine. Therefore, the preparation method of the present invention can be effectively used for functionalization or modification of a biomaterial.

In particular, as demonstrated in one embodiment of the present invention, when applying the preparation method of the present invention to rhEPO, functionalization (PEGylation in one embodiment of the present invention) selectively occurs only in the 49$^{th}$ tyrosine of rhEPO. According to the preparation method of the present invention, there is no side effect of generating a heterogeneous mixture of Mircera, the conventional PEGylated rhEPO drug, and selective functionalization of the protein occurs with an excellent yield. Therefore, the product of the present invention can be effectively used as a selectively PEGylated protein drug.

In another aspect of the present invention, the present invention provides a protein in which a compound represented by formula 2 is bound to —OH group of tyrosine of the biomaterial containing tyrosine present on the surface in an aqueous solution.

[Formula 2]

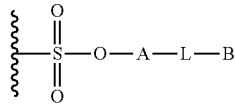

(In formula 2,

A is nonsubstituted or substituted $C_{6-14}$ arylene or 5-20 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, NR$^3$, —NHC(=O)—, —C(=O)NH— and straight or branched $C_{1-10}$ alkylene, or a combination thereof, and R$^3$ is hydrogen or straight or branched $C_{1-3}$ alkyl; and B is a compound for imparting functionality to a biomaterial).

A is nonsubstituted or substituted $C_{6-10}$ arylene or 5-15 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-3}$ alkyl, straight or branched $C_{1-3}$ alkoxy, =O and —OH.

A can be phenylene, xanthine or coumarin.

B is a compound for imparting functionality to a biomaterial. The compound may mean a biocompatible polymer. In addition, the compound for imparting functionality to the biomaterial can be an organic or inorganic fluorescent substance. The organic fluorescent substance can be rhodamine. To impart functionality to the biomaterial means to impart specific functionality to the biomaterial (functionalization), such as functionalization of the biomaterial itself (e.g., PEGylation), attachment of antibodies or complements, and attachment of fluorescent substances, and B can be used without restrictions as long as it makes this possible.

As an example, B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly (alkyl methacylate) having a weight average molecular weight of 100 to 50000, and peptide polymers having a weight average molecular weight of 100 to 50000, wherein alkoxy can be straight or branched $C_{1-10}$ alkoxy, alkylene can be straight or branched $C_{1-10}$ alkylene, and alkyl can be straight or branched $C_{1-10}$ alkyl.

B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly(alkyl methacylate) having a weight average molecular weight of 100 to 50000, and peptide polymers having a weight average molecular weight of 100 to 50000, wherein alkoxy can be straight or branched $C_{1-5}$ alkoxy, alkylene can be straight or branched $C_{1-5}$ alkylene, and alkyl can be straight or branched $C_{1-5}$ alkyl.

B is alkoxy or hydroxypolyalkyleneoxide having a weight average molecular weight of 100 to 50000, wherein alkoxy can be straight or branched $C_{1-3}$ alkoxy, and alkylene can be straight or branched $C_{1-3}$ alkylene.

B can be methoxy polyethyleneoxide having a weight average molecular weight of 100 to 50000.

In the B, the peptide polymer can be a polymer randomly bound with one or more amino acids selected from the natural amino acid group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine and tryptophan.

The weight average molecular weight of B can be 100 to 50000.

The weight average molecular weight of B can be 500 to 40000.

The weight average molecular weight of B can be 1000 to 30000.

At this time, the weight average molecular weight may vary depending on the weight average molecular weight of the B starting material used in the preparation of the compound represented by formula 1.

L can be any one selected from the group consisting of S, O, NR$^3$, —NHC(=O)—, —C(=O)NH— and straight or branched $C_{1-5}$ alkylene, or a combination thereof, and R$^3$ can be hydrogen or straight or branched $C_{1-3}$ alkyl.

L can be any one selected from the group consisting of —NHC(=O)—, —C(=O)NH— and straight or branched $C_{1-5}$ alkylene, or a combination thereof.

The protein is not limited as long as it is a biomaterial containing tyrosine present on the surface in an aqueous solution, but can be erythropoietin (EPO), chymotrypsinogen A, or activated chymotrypsin.

The tyrosine can be 49$^{th}$ tyrosine of EPO (erythropoietin).

According to an embodiment of the present invention, the compound represented by formula 2 selectively binds only to the outer surface of rhEPO (recombinant human EPO (erythropoietin)), that is, Tyr-49 present in an aqueous solution. In addition, none of the internal tyrosine residues bind to the compound (see Experimental Example 3 and Tables 3 and 4).

In addition, according to an embodiment of the present invention, the compound represented by formula 2 selectively binds only to Tyr-49 present in an aqueous solution, and thus which maintains the hematopoietic function, an inherent function of EPO (see Experimental Example 4 and FIG. 6).

Therefore, the protein to which the compound represented by formula 2 of the present invention is bound is selectively bound to tyrosine of the protein containing tyrosine present on the surface in an aqueous solution. In particular, functionalization (PEGylation in one embodiment of the present invention) selectively occurs only in the 49$^{th}$ tyrosine of rhEPO, so there is no side effect of generating a heterogeneous mixture of Mircera, the conventional PEGylated rhEPO drug, and selective functionalization of the protein occurs with an excellent yield. Therefore, the product of the present invention can be effectively used as a selectively PEGylated protein drug.

Thus, the protein to which the compound represented by formula 2 is bound can be used as a pharmaceutical composition comprising the same as an active ingredient.

In another aspect of the present invention, the present invention provides a method for PEGylating a biomaterial comprising a step of reacting a compound represented by formula 1 and a biomaterial containing tyrosine present on the surface in an aqueous solution in the presence of a compound represented by formula 3.

[Formula 1]

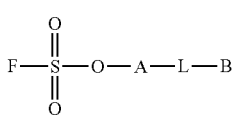

(In formula 1,

A is nonsubstituted or substituted $C_{6-14}$ arylene or 5-20 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, NR$^3$, —NHC(=O)—, —C(=O)NH— and straight or branched $C_{1-10}$ alkylene, or a combination thereof, and R$^3$ is hydrogen or straight or branched $C_{1-3}$ alkyl; and B is alkoxy or hydroxy polyalkyleneoxide having a weight average molecular weight of 100 to 50000, wherein alkoxy is straight or branched $C_{1-10}$ alkoxy, and alkylene is straight or branched $C_{1-10}$ alkylene);

[Formula 3]

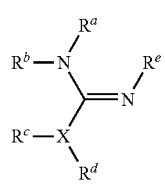

(In formula 3,

X is N or CH; and

R$^a$, R$^b$, R$^c$, R$^d$ and R$^e$ are independently hydrogen or straight or branched $C_{1-5}$ alkyl, R$^a$ and R$^e$ can form 5-8 membered heterocycloalkenyl along with N to which they are attached, and R$^b$ and R$^c$ can form 5-8 membered heterocycloalkyl along with N and X to which they are attached).

A is nonsubstituted or substituted $C_{6-10}$ arylene or 5-15 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-3}$ alkyl, straight or branched $C_{1-3}$ alkoxy, =O and —OH.

A can be phenylene, xanthine or coumarin.

B is alkoxy or hydroxypolyalkyleneoxide having a weight average molecular weight of 100 to 50000, wherein alkoxy can be straight or branched $C_{1-3}$ alkoxy, and alkylene can be straight or branched $C_{1-3}$ alkylene.

B can be methoxy polyethyleneoxide having a weight average molecular weight of 100 to 50000.

The weight average molecular weight of B can be 100 to 50000.

The weight average molecular weight of B can be 500 to 40000.

The weight average molecular weight of B can be 1000 to 30000.

At this time, the weight average molecular weight may vary depending on the weight average molecular weight of the B starting material used in the preparation of the compound represented by formula 1.

L can be any one selected from the group consisting of S, O, NR$^3$, —NHC(=O)—, —C(=O)NH— and straight or branched $C_{1-5}$ alkylene, or a combination thereof, and R$^3$ can be hydrogen or straight or branched $C_{1-3}$ alkyl.

L can be any one selected from the group consisting of —NHC(=O)—, —C(=O)NH— and straight or branched $C_{1-5}$ alkylene, or a combination thereof.

In the compound represented by formula 3, when X is N, the compound represented by formula 3 may be a guanidine derivative. In addition, R$^b$, R$^c$, R$^d$ and R$^e$ are independently hydrogen or straight or branched $C_{1-3}$ alkyl. Further, R$^a$, R$^b$, R$^c$, R$^d$ and R$^e$ are independently hydrogen or methyl.

When X is CH, the compound represented by formula 3 may be an amidine derivative. R$^a$, R$^b$, R$^c$, R$^d$ and R$^e$ are independently hydrogen or straight or branched $C_{1-3}$ alkyl, R$^a$ and R$^e$ can form 6 membered heterocycloalkenyl along with N to which they are attached, and R$^b$ and R$^c$ can form 7 membered heterocycloalkyl along with N and X(CH) to which they are attached.

R$^a$, R$^b$, R$^c$, R$^d$ and R$^e$ are independently hydrogen or methyl.

The compound represented by formula 3 can be DBU (1,8-Diazabicyclo(5.4.0)undec-7-ene) or TMG(1,1,3,3-tetramethylguanidine).

The compound represented by formula 3 can be TMG (1,1,3,3-tetramethylguanidine).

In another aspect of the present invention, the present invention provides a composition for hematopoiesis comprising EPO (erythropoietin), a biomaterial containing tyrosine present on the surface in an aqueous solution, to which a compound represented by formula 2 is bound to —OH group of the tyrosine as an active ingredient.

[Formula 2]

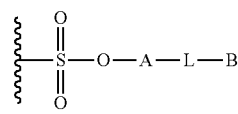

(In formula 2,

A is nonsubstituted or substituted $C_{6-14}$ arylene or 5-20 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, and $R^3$ is hydrogen or straight or branched $C_{1-3}$ alkyl; and B is a compound for imparting functionality to a biomaterial).

A is nonsubstituted or substituted $C_{6-10}$ arylene or 5-15 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-3}$ alkyl, straight or branched $C_{1-3}$ alkoxy, =O and —OH.

A can be phenylene, xanthine or coumarin.

B is a compound for imparting functionality to a biomaterial. The compound may mean a biocompatible polymer. In addition, the compound for imparting functionality to the biomaterial can be an organic or inorganic fluorescent substance. The organic fluorescent substance can be rhodamine. To impart functionality to the biomaterial means to impart specific functionality to the biomaterial (functionalization), such as functionalization of the biomaterial itself (e.g., PEGylation), attachment of antibodies or complements, and attachment of fluorescent substances, and B can be used without restrictions as long as it makes this possible.

As an example, B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly(alkyl methacylate) having a weight average molecular weight of 100 to 50000, and peptide polymers having a weight average molecular weight of 100 to 50000, wherein alkoxy can be straight or branched $C_{1-10}$ alkoxy, alkylene can be straight or branched $C_{1-10}$ alkylene, and alkyl can be straight or branched $C_{1-10}$ alkyl.

B is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly(alkyl methacylate) having a weight average molecular weight of 100 to 50000, and peptide polymers having a weight average molecular weight of 100 to 50000, wherein alkoxy can be straight or branched $C_{1-5}$ alkoxy, alkylene can be straight or branched $C_{1-5}$ alkylene, and alkyl can be straight or branched $C_{1-5}$ alkyl.

B is alkoxy or hydroxypolyalkyleneoxide having a weight average molecular weight of 100 to 50000, wherein alkoxy can be straight or branched $C_{1-3}$ alkoxy, and alkylene can be straight or branched $C_{1-3}$ alkylene.

B can be methoxy polyethyleneoxide having a weight average molecular weight of 100 to 50000.

In the B, the peptide polymer can be a polymer randomly bound with one or more amino acids selected from the natural amino acid group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine and tryptophan.

The weight average molecular weight of B can be 100 to 50000.

The weight average molecular weight of B can be 500 to 40000.

The weight average molecular weight of B can be 1000 to 30000.

At this time, the weight average molecular weight may vary depending on the weight average molecular weight of the B starting material used in the preparation of the compound represented by formula 1.

L can be any one selected from the group consisting of S, O, $NR^3$, —NHC(=O)—, —C(=O)NH— and straight or branched $C_{1-5}$ alkylene, or a combination thereof, and $R^3$ can be hydrogen or straight or branched $C_{1-3}$ alkyl.

L can be any one selected from the group consisting of —NHC(=O)—, —C(=O)NH— and straight or branched $C_{1-5}$ alkylene, or a combination thereof.

The tyrosine can be $49^{th}$ tyrosine of EPO (erythropoietin).

According to an embodiment of the present invention, the compound represented by formula 2 selectively binds only to the outer surface of rhEPO (recombinant human EPO (erythropoietin)), that is, Tyr-49 present in an aqueous solution. In addition, none of the internal tyrosine residues bind to the compound (see Experimental Example 3 and Tables 3 and 4).

In addition, according to an embodiment of the present invention, the compound represented by formula 2 selectively binds only to Tyr-49 present in an aqueous solution, and thus which maintains the hematopoietic function, an inherent function of EPO (see Experimental Example 4 and FIG. 6).

Therefore, in the composition for hematopoiesis of the present invention comprising EPO to which a compound represented by formula 2 is bound as an active ingredient, functionalization (PEGylation in one embodiment of the present invention) selectively occurs only in the $49^{th}$ tyrosine of hEPO, so there is no side effect of generating a heterogeneous mixture of Mircera, the conventional PEGylated rhEPO drug, and selective functionalization of the protein occurs with an excellent yield. Therefore, the composition of the present invention can be effectively used as a selectively PEGylated protein drug.

The composition for hematopoiesis can be used for the treatment or prevention of hematopoietic function-related diseases such as anemia, lymphocytic leukemia, myeloid leukemia, myeloma, idiopathic thrombocytopenic purpura, thrombocytopenia, hemophilia, von Willebrand disease, disseminated intravascular coagulation syndrome, nonspecific lymphadenitis, tuberculous lymphadenitis, sartoidosis, necrotizing lymphadenitis, Hodgkin lymphoma, non-Hodgkin lymphoma, splenomeglay and thymoma.

At this time, the anemia can be caused by renal failure.

The anemia can be caused by a disease that requires regular peritoneal dialysis or hemodialysis.

The composition for hematopoiesis can be used as a pharmaceutical composition for hematopoietic function-related diseases.

The pharmaceutical composition can be administered by parenterally and the parenteral administration includes subcutaneous injection, intravenous injection, intramuscular injection or intrathoracic injection.

To prepare the composition as a formulation for parenteral administration, the compound represented by formula 2 or the pharmaceutically acceptable salt thereof of the present invention is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a method for preventing or treating hematopoietic function-related diseases comprising a step of administering the composition for hematopoiesis comprising EPO (erythropoietin) containing tyrosine present on the surface in an aqueous solution to which a compound represented by formula 2 is bound to —OH group of the tyrosine as an active ingredient to a subject in need.

In another aspect of the present invention, the present invention provides a use of the composition for hematopoiesis comprising EPO (erythropoietin) containing tyrosine present on the surface in an aqueous solution to which a compound represented by formula 2 is bound to —OH group of the tyrosine as an active ingredient for the treatment or prevention of hematopoietic function-related diseases.

MODE FOR INVENTION

Hereinafter, the present invention will be described in detail by the following examples and experimental examples.

However, the following examples and experimental examples are only for illustrating the present invention, and the contents of the present invention are not limited thereto.

<Preparative Example 1> Preparation of 2,5-dioxopyrrolidine-1-yl 4-((fluorosulfonyl)oxy)benzoate

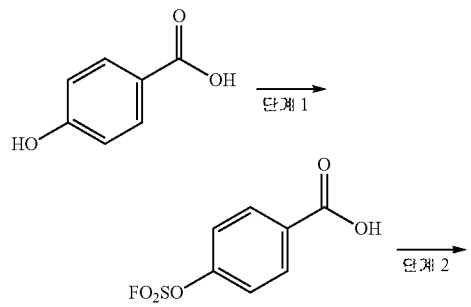

-continued

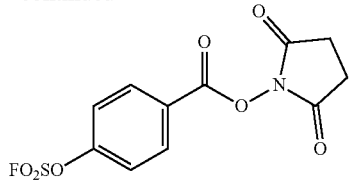

Step 1: Preparation of 4-((fluorosulfonyl)oxy)benzoic Acid

DCM (dichloromethane) containing 4-hydroxy benzoic acid (276 mg, 2.0 mmol) and TEA (trimethylamine) (1.1 mL, 8.0 mmol) was stirred for 12 hours under sulfuryl fluoride atmosphere. The mixture was poured into 1 N HCl solution and extracted with DCM. The organic layer was dried over $MgSO_4$ and purified by column chromatography (EA/Hex) to give 4-((fluorosulfonyl)oxy)benzoic acid as a yellow solid (114 mg, 26.0%).

$^1$H NMR (CDCl$_3$, 400 MHz): 10.19 (br s, 1H), 8.19 (d, J=8.0 Hz, 2H), 7.42 (d, J=12.0 Hz, 2H). $^{13}$C NMR (CDCl$_3$, 125 MHz): 169.68, 153.41, 132.69, 128.66, 121.09. $^{19}$F NMR (CDCl$_3$, 400 MHz): 38.77. LRMS (ESI) m/z: Anal. calcd. For [M−H]$^-$ C$_7$H$_4$FOS: 218.98; found: 218.95.

Step 2: Preparation of 2,5-dioxopyrrolidine-1-yl 4-((fluorosulfonyl)oxy)benzoate Anhydrous THF (tetrahydrofuran) containing the compound (113 mg, 0.51 mmol) prepared in step 1 above, N-hydroxysuccinimide (226 mg, 2.0 mmol) and N,N'-dicyclohexylcarbodiimide (117 mg, 0.57 mmol) was stirred for 12 hours. The mixture was evaporated and purified by column chromatography (EA/Hex) to give 2,5-dioxopyrrolidine-1-yl 4-((fluorosulfonyl)oxy)benzoate as a white solid (150 mg, 92.2%).

$^1$H NMR (CDCl$_3$, 300 MHz): 8.31 (d, J=9.0 Hz, 2H), 7.54 (d, J=9.0 Hz, 2H), 2.94 (s, 3H). $^{13}$C NMR (CDCl$_3$, 75 MHz): 168.96, 160.43, 153.95, 133.13, 128.64, 121.65, 25.66. $^{19}$F NMR (CDCl$_3$, 300 MHz): 39.32. LRMS (ESI) m/z: Anal. calcd. For [M+K]$^+$ C$_{11}$H$_8$FNO$_7$SK: 355.96; found: 356.2.

<Preparative Example 2> Preparation of Methoxy Polyethylene Glycol Amine

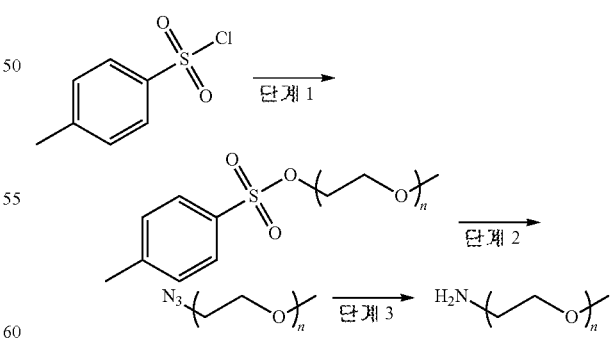

Step 1: Preparation of Methoxy Polyethylene Glycol Tosylate

DCM containing methoxy polyethylene glycol-2000 (MPEG-2000, 2.3 g, 1.15 mmol), TsCl (0.40 g, 2.1 mmol)

and TEA (0.40 mL, 2.9 mmol) was stirred overnight at 50° C. The mixture was poured into 1 N NaOH solution and extracted with DCM. The organic layer was washed with 1 N HCl 20 solution and dried over $MgSO_4$. The residue was dissolved in a small amount of DCM and precipitated using ethyl ether to give methoxy polyethylene glycol tosylate as a white solid (1.56 g, 63.2%).

Step 2: Preparation of Methoxy Polyethylene Glycol Azide

DMF (dimethyl formamide) containing the compound (400 mg, 0.19 mmol) prepared in step 1 above, sodium azide (24.2 mg, 0.37 mmol) and sodium bicarbonate (23.5 mg, 0.28 mmol) was stirred at 120° C. for 12 hours. After completely evaporating the solvent, the mixture was poured into 1 N NaOH solution, and extracted with DCM. The organic layer was dried over $MgSO_4$. The residue was dissolved in a small amount of DCM and precipitated using ethyl ether to give methoxy polyethylene glycol azide as a yellow solid (363 mg, 96.4%).

Step 3: Preparation of Methoxy Polyethylene Glycol Amine

Anhydrous THF (tetrahydrofuran) containing the compound (363 mg, 0.18 mmol) prepared in step 2 above and triphenylphosphine (70.5 mg, 0.27 mmol) was stirred for 12 hours. 100 L of water was added thereto, followed by stirring for 12 hours. After completely evaporating the solvent, 0.5 N NaOH solution was poured and extracted with DCM. The organic layer was dried over $MgSO_4$ and evaporated. The residue was dissolved in a small amount of DCM and precipitated using ethyl ether. The precipitate was washed with hexane to give methoxy polyethylene glycol amine as a white solid (278 mg, 77.3%).

$^1$H NMR ($CDCl_3$, 400 MHz): 3.83-3.49 (m, ~180H), 3.38 (s, 3H), 2.86 (t, J=4.0 Hz, 2H).

<Preparative Example 3> Preparation of 4-(methoxy polyethylene glycol carbamoyl)phenyl Sulfurofluoridate

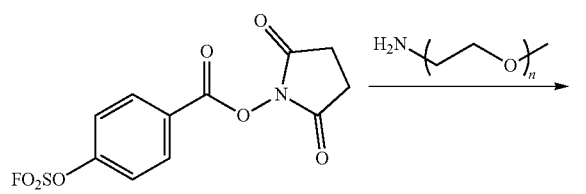

Anhydrous THF (tetrahydrofuran) containing the compound (17.5 mg, 0.055 mmol) prepared in Preparative Example 1, the compound (100 mg, 0.05 mmol) prepared in Preparative Example 2 and TEA (14 μL, 0.1 mmol) was stirred for 12 hours. The mixture was poured into 1 N HCl solution and extracted with DCM. The organic layer was dried over $MgSO_4$ and evaporated. The residue was dissolved in a small amount of DCM and precipitated using ethyl ether to give 4-(methoxy polyethylene glycol carbamoyl)phenyl sulfurofluoridate as a yellow solid (102 mg, 92.7%).

$^1$H NMR ($CDCl_3$, 400 MHz): 7.99 (d, J=8.0 Hz, 2H), 7.41 (d, J=8.0 Hz, 2H), 3.83-3.45 (m, ~180H), 3.38 (s, 3H). $^{19}$F NMR ($CDCl_3$, 300 MHz): 38.36.

<Preparative Example 4> Preparation of (2S,2'S)-3,3'-((sulfonylbis(oxy))bis(4,1-phenylene))bis(2-aminopropanoic Acid)

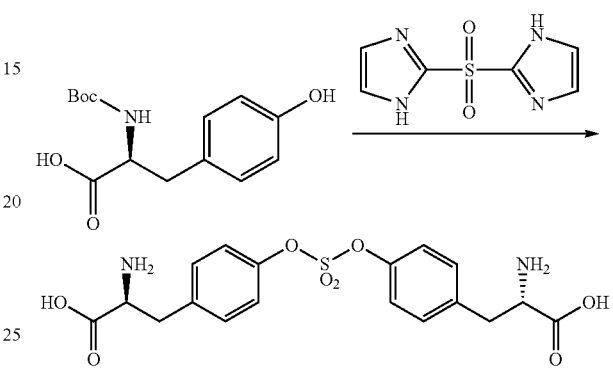

DMF (dimethyl formamide) containing N-Boc-L-tyrosine (118 mg, 0.42 mmol), sulfonyl diimidazole (40 mg, 0.2 mmol) and cesium carbonate (391 mg, 1.2 mmol) was stirred at 60° C. for 12 hours. The mixture was poured into 1 N HCl solution, and extracted with DCM. The organic layer was dried over $MgSO_4$ and evaporated. The residue was dissolved in DCM containing 30% TFA (trifluoroacetic acid solution), followed by stirring for 2 hours.

After evaporating the solvent and TFA using a rotary evaporator, the residue was purified by reversed phase HPLC (water/acetonitrile) to give (2S,2'S)-3,3'-((sulfonylbis(oxy))bis(4,1-phenylene))bis(2-aminopropanoic acid) as a white solid (29.5 mg, 2 step yield 34.8%).

$^1$H NMR ($CD_3OD$, 400 MHz): 7.42 (d, J=8.0 Hz, 4H), 7.32 (d, J=8.0 Hz, 4H), 4.13 (t, J=6.0 Hz, 2H), 3.33-3.30 (m, 2H), 3.18 (dd, J=6.0, 12.0 Hz, 2H), 2.13 (s, 2H). HRMS (ESI) m/z: Anal. calcd. For $[M+H]^+$ $C_{18}H_{21}N_2O_8S$: 425.10; found: 425.1016.

<Preparative Example 5> Preparation of N-(6-(diethylamino)-9-(2-((4-((fluorosulfonyl)oxy)phenetyl) carbamoyl)phenyl)-3H-xanthene-3-ylidene)-nethylethanaminium

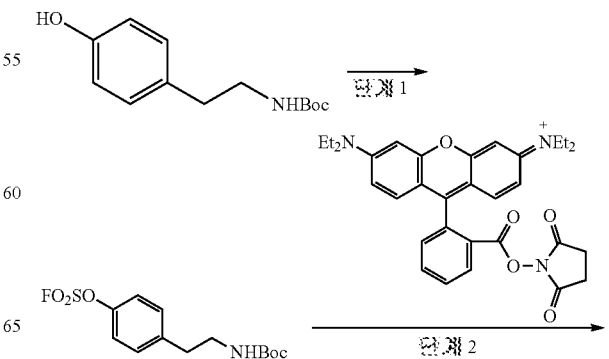

-continued

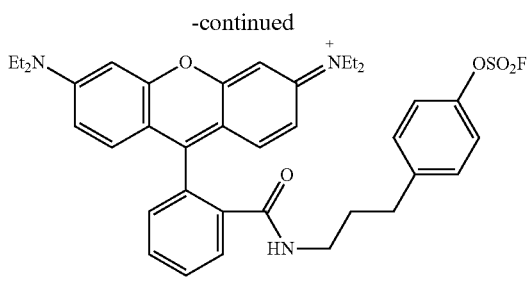

Step 1: Preparation of 4-(2-((tertbutoxycarbonyl)amino)ethyl)phenyl Sulfurofluoridate DCM (dichloromethane) containing N-Boc tyramine (0.13 g, 0.55 mmol) and triethylamine (0.24 mL, 1.69 mmol) was stirred at room temperature under $SO_2F2$ atmosphere. After 5 hours, the mixture was poured into distilled water and extracted with MC (methylene chloride). The organic layer was dried over $MgSO_4$ and purified by column chromatography (EA/Hex) to give 4-(2-((tert-butoxycarbonyl)amino)ethyl)phenyl sulfurofluoridate as a pale pink solid (145 mg, 82.9%).

$^1$H NMR ($CDCl_3$, 400 MHz): 7.26 (s, 4H), 4.53 (br s, 1H), 3.36 (d, J=8.0 Hz, 2H), 2.82 (t, J=8.0 Hz, 2H), 1.41 (s, 9H). 13C NMR (CDCl3, 100 MHz): 155.79, 148.61, 140.02, 130.66, 120.84, 79.37, 41.51, 35.65, 28.30. 19F NMR ($CDCl_3$, 400 MHz): 37.26. LRMS (ESI) m/z: Anal. calcd. For $[M+Na]^+$ $C_{13}H_{18}FNNaO_5S$: 342.08; found: 342.2.

Step 2: Preparation of N-(6-(diethylamino)-9-(2-((4-((fluorosulfonyl)oxy)phenetyl)carbamoyl)phenyl)-3H-xanthene-3-ylidene)-nethylethanaminium The compound (46.4 mg, 0.15 mmol) obtained in step 1 above was stirred in DCM solvent containing 10% TFA for 1 hour. The mixture was poured into 1 N NaOH solution in an ice bath, and extracted with MC. The organic layer was dried over $MgSO_4$. Tetraethylfluorescent substance succinimidyl ester (40 mg, 0.07 mmol) and triethylamine (20 μL, 0.14 mmol) were added thereto, followed by stirring in anhydrous DCM for 2 hours. The mixture was poured into brine, and extracted with MC. The organic layer was dried over $MgSO_4$ and purified by column chromatography (EA/Hex) to give N-(6-(diethylamino)-9-(2-((4-((fluorosulfonyl)oxy)phenetyl)carbamoyl)phenyl)-3H-xanthene-3-ylidene)-nethylethanaminium as a yellow oil (11 mg, 24.3%).

$^1$H NMR ($CDCl_3$, 500 MHz): 7.92 (t, J=5.0 Hz, 1H), 7.46 (dd, J=5.0 Hz, 2H), 7.13-7.06 (m, 5H), 6.41 (s, 3H), 6.39 (s, 1H), 6.24 (dd, J=2.5, 7.5 Hz, 2H), 3.33 (q, J=6.7 Hz, 8H), 3.29 (t, J=7.5 Hz, 2H), 2.53 (t, J=7.5 Hz, 2H), 1.17 (t, J=7.5 Hz, 12H). $^{13}$C NMR ($CDCl_3$, 125 MHz): 167.75, 153.46, 153.10, 148.81, 148.34, 140.47, 132.38, 131.54, 130.58, 128.94, 128.09, 123.83, 122.73, 120.48, 108.09, 105.61, 97.61, 64.96, 44.34, 41.67, 33.89, 29.70, 12.56. $^{19}$F NMR ($CDCl_3$, 300 MHz): 37.18. HRMS (ESI) m/z Anal. calcd. For $[M]^+$ $C_{36}H_{39}FN_3O_5S$: 644.26; found: 644.2593.

<Example 1> Preparation of PEG-rhEPO (PEGylated Recombinant Human Erythropoietin, PEG Mw=2000)

In order to prepare a recombinant human EPO (erythropoietin) conjugated with PEG (PEGylated rhEPO) by the preparation method according to the present invention, the following experiment was performed. A schematic diagram of the reaction is shown in FIG. 1. The residue (—OH) of tyrosine on the outer surface of EPO reacted with the fosylate PEG obtained in Preparative Example 3 to form a sulfate (—O—$SO_2$—O—) bond to tyrosine, and PEGylation occurred. The detailed preparation method is as follows, and the mass value was measured by MALDI-TOF MS. A MALDI-TOF MS measurement result graph of 4-(methoxy polyethylene glycol carbamoyl)phenyl sulfurofluoridate, a fosylate PEG starting material, is shown in FIG. 2, and the MALDI-TOF MS measurement result of the PEG-rhEPO in which PEG was introduced into rhEPO prepared in Example 1 is shown in FIG. 3. The MALDI-TOF MS measurement results of rhEPO before PEGylation and rhEPO after PEGylation (PEG-rhEPO) were compared and the results are shown in FIG. 4.

Particularly, 50 μL (4.63×10−4 μmol) of rhEPO stock solution (25 μg/100 μL) was dissolved in Tris buffer (50 mM, pH 8.0) (450 μL) containing 10 μL (4.63×10−2 μmol) of TMG stock solution (0.53 mg/1 mL) and 10 μL (2.32×10−3 μmol) of the compound fosylate PEG (the compound prepared in Preparative Example 3) (PEG-Fs; Mn=2,372, PD=1.004) (0.51 mg/mL), followed by reaction for 3 hours. The crude mixture was purified by repeated ultracentrifugation 5 times for 15 minutes at 14,000 rpm, and the buffer was replaced with DPBS (Dulbecco's Phosphate-Buffered Saline) 3 times using Amicon Ultra-0.5 devices.

LRMS (MALDI) m/z: Anal. calcd. for $[M+H]^+$: 28914.9; found 29170.8.

As shown in FIG. 4, the MALDI-TOF MS spectrum showed a clear shift of m/z, which was about 1980 Da, and the molecular weight was assumed to correspond to the molecular weight of the PEG PEGylated to rhEPO. Thus, it was confirmed that the desired PEGylated rhEPO was normally prepared.

Meanwhile, Mircera, a conventional PEGylated rhEPO drug, has a problem that most of the 7 lysine residues on the rhEPO surface react with Lys-45 or Lys-52, resulting in a heterogeneous mixture of the PEGylated rhEPO. However, the PEGylation method of the present invention targets the external tyrosine of rhEPO, and only one Tyr (Tyr-49) exists on the surface of rhEPO, so that a heterogeneous mixture as in Mircera is not generated.

According to the preparation method of the present invention, the binding reaction with other amino acids or tyrosine in the inside of a biomaterial (for example, the inside of a protein, the part that is not in contact with the aqueous solution) does not occur in an aqueous solution that is not present on the surface in the aqueous solution by selectively binding the compound represented by formula 2 to the tyrosine. Therefore, it can be effectively used for functionalization or modification of a biomaterial.

<Example 2> Preparation of PEG-rhEPO (PEGylated Recombinant Human Erythropoietin, PEG Mw=30K)

A PEGylated rhEPO was prepared in the same manner as described in Example 1, except that PEG having MW of 30000 was used. The fosylate PEG having MW of 30000 was prepared in the same manner as described in Preparative Example 3 and used. The MALDI-TOF MS measurement results of the prepared PEGylated rhEPO are shown in FIG. 8.

Particularly, 50 μL (4.63×10⁻⁵ mol) of rhEPO stock solution (25 μg/100 μL) was dissolved in Tris buffer (50 mM, pH 8.0) (45 μL) containing 1 μL (4.63×10-3 μmol) of TMG stock solution (0.53 mg/1 mL) and 4 μL (9.3×10−4 mol) of PEG30K (the compound prepared in the same manner as described in Preparative Example 3) (PEG30K-Fs; Mn=30, 841) (7.0 mg/mL), followed by reaction for 12 hours. The crude mixture was purified by repeated ultracentrifugation 5 times for 15 minutes at 14,000 rpm, and the buffer was replaced with DIW (deionized water) 3 times using Amicon Ultra-0.5 devices.

LRMS (MALDI) m/z: Anal. calcd. for [M+H]⁺: 59736; found: 54966.

FIG. 8 is a graph showing the MALDI-TOF MS measurement results of PEG-rhEPO of Example 2.

As shown in FIG. 8, the MALDI-TOF MS spectrum showed a clear shift of m/z, which was about 26021 Da, and the molecular weight was assumed to correspond to the molecular weight of the PEG30K PEGylated to rhEPO. Thus, it was confirmed that the desired PEGylated rhEPO was normally prepared.

In addition, it was confirmed from the results of Examples 1 and 2 that the structures and sizes of other substituents other than the fosylate group in which SuFEx reaction occurs did not significantly affect the preparation method of the present invention.

<Example 3> Preparation of Chymotrypsinogen a Introduced with Fluorescent Substance Rhodamine To verify whether the SuFEx modification is possible in proteins other than EPO of Examples 1 and 2, Rho-chymotrypsinogen A was prepared using the fosylate rhodamine phosphor obtained in Preparation Example 5.

Particularly, 10 μL (4.63×10⁻⁴ mol) of chymotrypsinogen stock solution (1 mg/842 μL) was dissolved in a solution containing 250 μL of DMSO and 250 L of Tris buffer (50 mM, pH 8.0). Then, 100 L (4.63×10⁻¹ mol) of TMG stock solution (0.53 mg/1 mL) was dissolved in the solution containing chymotrypsinogen. 0.197 μL (2.31×10-3 μmol) of the fosylate rhodamine stock solution (7.63 mg/1 mL) obtained in Preparative Example 5 dissolved in DMSO was dissolved in the solution containing chymotrypsinogen, followed by stirring for 12 hours. The crude mixture was purified by repeated ultracentrifugation 4 times for 15 minutes at 14,000 rpm, and the buffer was replaced with DIW (deionized water) 4 times using Amicon Ultra-0.5 devices.

LRMS (MALDI) m/z: Anal. calcd. for [M]:26377.1; found: 26391.1.

FIG. 9 is a set of graphs showing the MALDI-TOF MS measurement results of chymotrypsinogen without rhodamine (FIG. 9a) and the MALDI-TOF MS measurement results of chymotrypsinogen with rhodamine of Example 3 (FIG. 9b).

As shown in FIG. 9, the MALDI-TOF MS spectrum showed a clear shift of m/z, which was about 26391.1 Da, and the molecular weight was assumed to correspond to the molecular weight of rhodamine linked to chymotrypsinogen. Thus, it was confirmed that the desired rhodamine-conjugated chymotrypsinogen was normally prepared.

In addition, it was confirmed from the results of Example 3 that the preparation method according to the present invention was not limited to the EPO of Example 1. Particularly, the reaction occurred without being limited to any biomaterial containing tyrosine present on the surface in an aqueous solution. Not only PEGylation but also the introduction of a fluorescent substance was possible. Thus, it was found that the reaction could occur without limitation as long as it was a compound having a fosylate group and a biomaterial containing tyrosine present on the surface in an aqueous solution.

<Experimental Example 1> Experiment to Find Optimal Base for SuFEx Reaction of —OH of Tyrosine and Phenyl Fosylate In the protein containing tyrosine on the outer surface, in order to find the optimal base condition for forming a sulfate bond (—O—SO₂—O—) through SuFEx reaction, an experiment was performed by adding 1 equivalent each in the same manner by varying only the base conditions in the reaction of phenyl fosylate and p-cresol, as shown in reaction formula A below. The results are shown in table 1 below.

[Reaction Formula A]

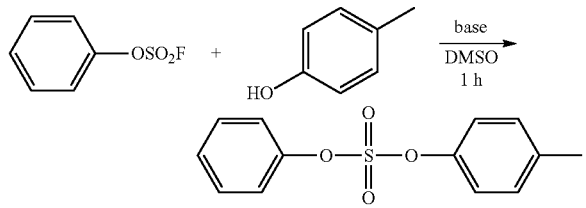

In reaction formula A, the base is a base selected from the group consisting of TEA (trimethylamine), DIPEA (diisopropylethylamine), imidazole, benzimidazole, DBU (1,8-Diazabicyclo[5.4.0]undec-7-ene) and TMG (tetramethylguanidine), and DMSO is dimethyl sulfoxide.

TABLE 1

| Entry | Base | Yield |
|---|---|---|
| 1 | TEA | n.d. |
| 2 | DIPEA | n.d. |
| 3 | Imidazole | n.d. |
| 4 | Benzimidazole | n.d. |
| 5 | DBU | Q.Y. |
| 6 | TMG | Q.Y. | n.d.: non detention
Q.Y.: quantitative yield

As shown in table 1 above, when DBU or TMG was used as a base, the reaction occurred in quantitative yield, so the compound having a desired sulfate bond could be prepared, but when other bases were used, the desired product was not synthesized at all.

In addition, when no base was used, the reaction did not proceed.

On the other hand, when DBU was used, the amino acid selectivity was inferior compared to when TMG was used.

Therefore, considering that the amino acid selectivity and the environment in which the biomaterial is present is an aqueous solution, it is more preferable to use TMG.

<Experimental Example 2> Evaluation of Results of SuFEx (Sulfur Fluoride Exchange) Reaction According to Nucleophile Bound to Amino Acid In the protein containing tyrosine on the outer surface, in order to evaluate whether the functionalization was selectively performed in the —OH group of tyrosine rather than other amino acids of the protein, SuFEx reaction of each nucleophile (residue) compound and phenyl fosylate in amino acids with different types of nucleophiles (residues) bound to the amino acids was performed, and the yield was measured, as shown in reaction formula B below. The results are shown in table 2 below.

Particularly, DMSO containing a nucleophile (10 mM), a phenyl fosylate compound and TMG was stirred, and the reaction progress was confirmed by GC-MS.

[Reaction Formula B]

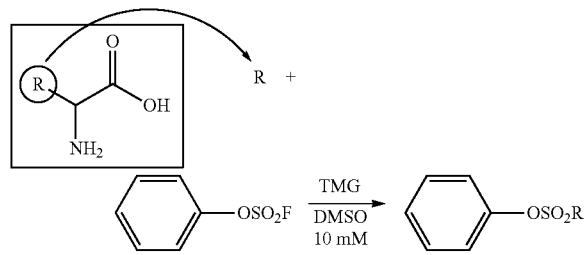

In reaction formula B,
R is p-cresol, n-butylamine, propanethiol, methanol, N-propylguanidine, 3-methylindole or 4-methylimidazole;
TMG is tetramethylguanidine; and
DMSO is dimethyl sulfoxide.

TABLE 2

| Entry | Nucleophile(R) | Amino acid | Reaction time (h) | Yield$^a$ |
|---|---|---|---|---|
| 1 | p-cresol | Tyrosine (Tyr) | 1.5 | 93.5 |
| 2 | n-butylamine | Lysine (Lys) | 12 | n.d. |
| 3 | propanethiol$^c$ | Cysteine (Cys) | 12 | n.d. |
| 4 | methanol | Serine (Ser) | 12 | n.d. |
| 5 | N-propylguanidine | Arginine (Arg) | 12 | n.d. |
| 6 | 3-methylindole | Tryptophan (Trp) | 12 | 12.5 |
| 7$^b$ | 4-methylimidazole | Histidine (His) | 12 | Trace |

$^a$yield of a separated material
$^b$add 0.25 equivalent of NiCl$_2$(H$_2$O)$_6$
$^c$In the nucleophile, in the case of cysteine, the nucleophile is methanethiol, but methanethiol is replaced with propanethiol for ease of handling because methanethiol is in a gaseous state.
n.d.: non detection As a result of the experiment, it was confirmed that only p-cresol was completely consumed among the several nucleophiles bound to amino acids, and when p-cresol was used at a higher concentration (0.1 M), the reaction was completed within 5 minutes.

As shown in table 2, in the case of p-cresol, the binding reaction occurred at the highest yield of 93.5%, and the reaction did not occur at all with other amino acid residues, or even if it occurred, the reaction proceeded slowly with a very low yield, indicating that SuFEx reaction occurred selectively with tyrosine.

Therefore, it was confirmed from the above results that the biomaterial to which the compound represented by formula 2 according to an aspect of the present invention is bound was selectively bound to tyrosine present on the surface in an aqueous solution.

<Experimental Example 3> Evaluation of Tryptic Digestion of Proteins

In order to determine the PEGylation site of the PEGylated rhEPO prepared in Example 1, an in-depth mass study was performed through trypsin digestion evaluation. Particularly, the experiment was performed as follows. The results of performing trypsin digestion evaluation with the non-PEGylated rhEPO (MALDI-TOF spectrum) are shown in FIG. 5a, and the result of performing trypsin digestion evaluation with the PEGylated rhEPO prepared in Example 1 (MALDI-TOF spectrum) are shown in FIG. 5b.

Trypsin is a proteolytic enzyme that cleaves K and R sites, and when there are overlapping amino acids such as KK, KR, RK, and RR in the protein to be cut, the mis-cleaved peptide form becomes the major result of trypsin digestion. Over time, it can become a full-cleaved peptide.

The tyrosine present on the surface of rhEPO is the 49$^{th}$ tyrosine, the mis-cleaved peptide with Y49 is VNFYAWKR, and the full-cleaved peptide is VNFYAWK. As a result of comparing the calculated m/z of the PEGylated peptide with the measured value, it was confirmed that they were a mis- and full-cleaved peptides. Since no PEGylated fragment other than these two was found, it can be seen that PEGylation was characteristically performed only in Y49.

In addition, after the trypsin treatment, the PEGylated m/z found values in the MALDI-TOF spectrum of the PEGylated rhEPO are shown in Tables 3 and 4 below. Table 3 shows the m/z found values of the mis-cleaved peptide VNFYAWKR, and Table 4 shows the m/z found values of the full-cleaved peptide VNFYAWK.

Particularly, trypsin digestion was performed with rhEPO and PEG-rhEPO through a modified method. More particularly, 12.5 g of rhEPO and PEG-rhEPO were dissolved in 30 L of DPBS. Trypsin protease was added thereto at the enzyme/substrate ratio of 1:20 (w/w), and the mixture was incubated at 37° C. for 3 hours.

TABLE 3

| n(# of PEG) | 15 | 16 | 17 | 18 | 19 | 20 | 21 | 22 | 23 | 24 |
|---|---|---|---|---|---|---|---|---|---|---|
| Expected | 1970.991 | 2015.018 | 2059.044 | 2103.07 | 2147.096 | 2191.122 | 2235.149 | 2279.175 | 2323.201 | 2367.227 |
| Observed | 1971.885 | 2015.838 | 2059.787 | 2103.762 | 2146.624 | 2191.638 | 2235.616 | 2279.585 | 2323.545 | 2367.508 |
| n(#of PEG) | 25 | 26 | 27 | 28 | 29 | 30 | 31 | 32 | 33 | 34 |
| Expected | 2411.254 | 2455.28 | 2499.306 | 2543.332 | 2587.358 | 2631.385 | 2675.411 | 2719.437 | 2763.463 | 2807.489 |
| Observed | 2411.456 | 2455.422 | 2499.375 | 2543.319 | 2587.292 | 2631.242 | 2675.204 | 2718.084 | 2763.122 | 2807.059 |

TABLE 4

| n(# of PEG) | 18 | 19 | 20 | 21 | 22 | 23 | 24 |
|---|---|---|---|---|---|---|---|
| Expected | 1946.969 | 1990.955 | 2035.021 | 2079.048 | 2123.074 | 2167.1 | 2211.126 |
| Observed | 1947.05 | 1990.996 | 2034.946 | 2078.901 | 2122.854 | 2166.805 | 2211.492 |
| n(#of PEG) | 25 | 26 | 27 | 28 | 29 | 30 | 31 |
| Expected | 2255.153 | 2299.179 | 2343.205 | 2387.231 | 2431.257 | 2475.284 | 2519.31 |
| Observed | 2254.748 | 2298.679 | 2342.61 | 2386.546 | 2430.476 | 2474.422 | 2518.322 |

As shown in FIG. 5, Table 3 and Table 4, it was confirmed that PEG was selectively bound only to Tyr-49 present on the outer surface of rhEPO. It was also confirmed that no PEGylation occurred in any of the internal Tyr residues. These results indicate that the structural integrity of EPO was maintained throughout the process of PEGylation. On the other hand, it was confirmed that PEGylation was not performed without additional additives such as $Ni^{2+}$ although some of the exposed amino acid residues (His-32 and His-94) existed on the outer surface of the EPO protein.

From the above results, it was confirmed that the PEGylation occurred selectively only in Tyr-49 present on the outer surface of EPO the functionalized protein characterized in that the functional group represented by formula 1 is bound to the —OH group of the tyrosine, in the protein containing tyrosine on the outer surface of the present invention, and no PEGylation occurred in other amino acid residues or tyrosine residues present in the inside of EPO.

It was also confirmed from the above results that the PEGylated rhEPO of the present invention had no side effect of generating a heterogeneous mixture of Mircera, the conventional PEGylated rhEPO drug, and the selective functionalization of the protein occurred with an excellent yield. Therefore, the PEGylated rhEPO of the present invention can be effectively used as a selectively PEGylated protein drug.

Therefore, the protein to which the compound represented by formula 2 of the present invention is bound was selectively bound to tyrosine of the protein containing tyrosine present on the surface in an aqueous solution. In particular, functionalization (PEGylation in one embodiment of the present invention) selectively occurred only in the $49^{th}$ tyrosine of rhEPO, so there was no side effect of generating a heterogeneous mixture of Mircera, the conventional PEGylated rhEPO drug, and the selective functionalization of the protein occurred with an excellent yield. Therefore, the protein of the present invention can be effectively used as a selectively PEGylated protein drug.

<Experimental Example 4> Evaluation of Protein Function of PEGylated rhEPO

In order to confirm whether the PEGylated rhEPO obtained in Example 1 maintained the hematopoietic function even after the PEGylation, the following experiment was performed, and the results are shown in FIG. 6.

The rhEPO without PEGylation and the PEGylated rhEPO (PEG-rhEPO) prepared in Example 1 were intravenously injected into Balb/c mice at a dose of 20 μg/kg every 3 days. In vivo activities were compared by measuring hematocrit (HCT), a reliable method for quantification of erythrocytes. As a control, phosphate buffered saline (PBS) was used.

Particularly, normal male Balb/c mice were purchased from Orient Bio Inc. (South Korea). The weight of the mice was 23-25 g, and the mice were housed in groups of 3-4 mice in one cage. Food and water were supplied freely (ad libitum), and each cage was allowed to have a 12-hour light/dark cycle under the conventional animal experiment system of KPC, Korea.

Each sample (rhEPO or PEG-rhEPO) (0.16 M in DPBS) was injected intravenously into normal male Balb/c mice (50 μL/mouse) every 3 days for 2 weeks. The same amount of DPBS was administered to the control group. A total of 21 mice were used in the experiment. Blood samples were collected every 3 days including day 0 to evaluate the hematopoietic effect. Hematocrit was evaluated by measuring the volume of the packed cells obtained by centrifugation performed immediately after the blood collection. Delta hematocrit (DHematocrit) was determined by the difference between the initial hematocrit for each mouse (day 0) and the hematocrit at each time point.

As shown in FIG. 6, through the periodic collection of samples for 15 days, it was confirmed that the HCT level (ΔHCT=–2-5%) of the control group was significantly decreased. On the other hand, the HCT level of the PEGylated rhEPO (PEG-rhEPO) was increased for 15 days. In addition, the rhEPO without PEGylation showed an increase trend similar to that of the PEG-rhEPO.

As a result of statistical analysis, it was confirmed that there was a clear difference between the HCT levels of the control group and the PEG-rhEPO, and there was no significant difference between the HCT levels of the PEG-rhEPO and the rhEPO without PEGylation.

Therefore, it was confirmed that the PEGylated rhEPO of the present invention can be used as a drug because it maintained its normal intrinsic hematopoietic function even after PEGylation.

<Experimental Example 5> Evaluation of Cytotoxicity of Aryl Compound Containing Sulfate The following experiment was performed to confirm whether the protein PEGylated with sulfate bond (—O—$SO_2$—O—) exhibits cytotoxicity. The cytotoxicity was evaluated in HeLa cells by cell counting kit-8 (CCK-8) viability test. The results were calculated by the following mathematical formula 1 and shown in FIG. 7.

[Mathematical Formula 1]

$$\text{Cell viability (\%)} = \frac{Absorbance_{treated} - Absorbance_{background}}{Absorbance_{untreated} - Absorbance_{background}} \times 100$$

Particularly, HeLa cells were seeded in a 96-well tissue culture plate at the density of 5,000 cells/well and cultured in 100 μL of DMEM (Dulbecco's Modified Eagle's Medium) supplemented with 10% FBS (fetal bovine serum) for 24 hours. After replacing the medium with 90 μL of a fresh medium, 10 μl of the compound prepared in Preparative Example 4 of various concentrations (final 0.5% DMSO) was added to each well of the plate, and the cells were further cultured for 24 hours and 48 hours. The cells were washed 3 times with a fresh medium to remove extracellular samples, and 100 μl of a fresh medium containing 10% CCK-8 was added to each well of the plate. After incubating the cells at 37° C. for 2 hours, $OD_{450}$ was measured with a microplate reader (Molecular Devices Co., Menlo Park, Calif., USA). Only the background signal of CCK-8 was subtracted from all the samples. The cell viability was evaluated as the percentage of absorbance of the untreated cells to the control.

As shown in FIG. 7, it was confirmed that the compound of the present invention did not show cytotoxicity even after 24 hours and 48 hours when the compound was treated at the concentrations of 0.1 to 100 μM.

Therefore, it was confirmed through the above results that the PEGylated biomaterial had no cytotoxicity, and it can be effectively used as a drug.

According to the preparation method of the present invention, the binding reaction with other amino acids or tyrosine in the inside of a biomaterial (for example, the inside of a protein, the part that is not in contact with the aqueous solution) does not occur in an aqueous solution that is not present on the surface in the aqueous solution by selectively binding the compound represented by formula 2 to the tyrosine. Therefore, the preparation method of the present invention can be effectively used for functionalization or modification of a biomaterial.

In addition, the protein to which the compound represented by formula 2 of the present invention is coupled is selectively bound to tyrosine of the protein containing tyrosine present on the surface in an aqueous solution. In particular, functionalization (PEGylation in one embodiment of the present invention) selectively occurs only in the 49$^{th}$ tyrosine of rhEPO, so there is no side effect of generating a heterogeneous mixture of Mircera, the conventional PEGylated rhEPO drug, and selective functionalization of the protein occurs with an excellent yield. Therefore, the protein of the present invention can be effectively used as a selectively PEGylated protein drug.

INDUSTRIAL APPLICABILITY

The manufacturing method of the present invention can be usefully used for functionalization or modification of a biological material.

In addition, the protein to which the compound represented by Formula 2 of the present invention is bound can be usefully used as a selectively PEGylated protein drug.

The invention claimed is:

1. A method for preparing a biomaterial to which a compound represented by Formula 2 is coupled, comprising a step of reacting a compound represented by Formula 1 and a biomaterial containing a tyrosine residue present on an outer surface of the biomaterial in an aqueous solution in the presence of a compound represented by Formula 3, wherein the compound represented by Formula 2 selectively binds to the tyrosine residue present on the outer surface of the biomaterial and the biomaterial is a protein:

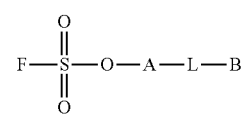

[Formula 1]

wherein in Formula 1, A is nonsubstituted or substituted $C_{6-14}$ arylene or 5-20 membered nonsubstituted or substituted heteroarylene, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, and $R^3$ is hydrogen or straight or branched $C_{1-3}$ alkyl; and B is a compound for imparting functionality to a biomaterial;

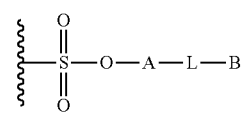

[Formula 2]

wherein in Formula 2, A, L and B are as defined in Formula 1 and the vertical line left of the sulfur atom indicates that the sulfur atom is bonded to the biomaterial;

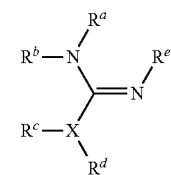

[Formula 3]

wherein in Formula 3, X is N; and $R^a$, $R^b$, $R^c$, $R^d$ and $R^e$ are independently hydrogen or straight or branched $C_{1-5}$ alkyl, $R^a$ and $R^e$ can form 5-8 membered heterocycloalkenyl along with N to which they are attached, and Rb and RC can form **5-8 membered heterocycloalkyl along with N and X to which they are attached.

2. The method for preparing a biomaterial according to claim 1, wherein the A is nonsubstituted or substituted $C_{6-10}$ arylene or 5-15 membered nonsubstituted or substituted heteroarylene containing one or more hetero atoms selected from the group consisting of N, O and S, wherein the substituted arylene and heteroarylene can be substituted with one or more selected from the group consisting of halogen, straight or branched $C_{1-3}$ alkyl, straight or branched $C_{1-3}$ alkoxy, =O and —OH.

3. The method for preparing a biomaterial according to claim 1, wherein the A is phenylene, xanthine or coumarin.

4. The method for preparing a biomaterial according to claim 1, wherein the B is a compound for imparting functionality to a biomaterial, which is any one selected from the group consisting of alkoxy or hydroxypolyalkyleneoxide having a weight average molecular weight of 100 to 50000, poly(2-alkyl methacryloyloxyethyl phosphorylcholine) having a weight average molecular weight of 100 to 50000, poly(alkyl methacylate) having a weight average molecular weight of 100 to 50000, and peptide polymers having a weight average molecular weight of 100 to 50000, wherein alkoxy is straight or branched $C_{1-10}$ alkoxy, alkylene is straight or branched $C_{1-10}$ alkylene, and alkyl is straight or branched $C_{1-10}$ alkyl.

5. The method for preparing a biomaterial according to claim 4, wherein the peptide polymer is a polymer randomly bound with one or more amino acids selected from the natural amino acid group consisting of valine, leucine, isoleucine, methionine, phenylalanine, asparagine, glutamic acid, aspartic acid, glycine, alanine, serine, threonine, cysteine, proline, glutamine, histidine, lysine, arginine, tyrosine and tryptophan.

6. The method for preparing a biomaterial according to claim 1, wherein the compound for imparting functionality to the biomaterial is an organic or inorganic fluorescent substance.

7. The method for preparing a biomaterial according to claim 1, wherein the compound represented by Formula 3 is a tetramethylguanidine.

8. The method for preparing a biomaterial according to claim 1, wherein the protein is selected from the group consisting of peptides, peptidomimetics, antibodies, enzymes, peptide-based hormones and complements, antibody-drug conjugates, protein-polymer conjugates, and fluorescent proteins.

9. The method for preparing a biomaterial according to claim 1, wherein the biomaterial is EPO (erythropoietin), chymotrypsinogen A or activated chymotrypsin.

10. The method for preparing a biomaterial according to claim 1, wherein the L is any one selected from the group consisting of —NHC(=O)—, —C(=O)NH— and straight or branched $C_{1-5}$ alkylene, or a combination thereof.

11. The method for preparing a biomaterial according to claim 1, wherein the method is conducted by further adding a polar solvent selected from the group consisting of $C_{1-5}$ lower alcohols and DMSO (dimethyl sulfoxide) to react.

12. The method according to claim 1,
wherein B is alkoxy or hydroxy polyalkyleneoxide having a weight average molecular weight of 100 to 50000, wherein alkoxy is straight or branched $C_{1-10}$ alkoxy, and alkylene is straight or branched $C_{1-10}$ alkylene.

13. The method according to claim 9, wherein the biomaterial is EPO, and the compound represented by Formula 2 is bound to an —OH group of the tyrosine of the EPO.

14. The method according to claim 13, wherein the tyrosine residue is the $49^{th}$ tyrosine residue of EPO.

15. The method according to claim 9, wherein EPO is human recombinant EPO (rhEPO).

16. The method of claim 15, wherein A is phenylene, L is —C(=O)NH—, and B is methoxy polyethylene glycol 2000.

17. The method of claim 16, wherein $R^a$, $R^b$, $R^c$, and $R^d$ are methyl, and $R^e$ is hydrogen.

18. A method for preparing erythropoietin (EPO) to which a compound represented by Formula 1 is coupled only to a tyrosine of EPO, comprising reacting a compound represented by Formula 1 and EPO in an aqueous solution in the presence of 1,1,3,3-tetramethylguanidine (TMG):

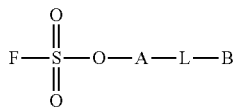

[Formula 1]

wherein A is nonsubstituted or substituted $C_{6-14}$ arylene or 5-20 membered nonsubstituted or substituted heteroarylene, wherein the substituted arylene and heteroarylene can be substituted with one or more selected from the group consisting of halogen, straight or branched $C_{1-5}$ alkyl, straight or branched $C_{1-5}$ alkoxy, =O and —OH;

L is any one selected from the group consisting of S, O, $NR^3$, —NHC(=O)—, —C(=O)NH— and straight or branched $C_{1-10}$ alkylene, or a combination thereof, and $R^3$ is hydrogen or straight or branched $C_{1-3}$ alkyl; and B is a biocompatible polymer, organic or inorganic fluorescent substance, or an antibody.

19. The method of claim 18, wherein A is phenylene, L is —C(=O)NH—, and B is methoxy polyethylene glycol 2000.

20. The method of claim 18, wherein the compound represented by Formula 1 is coupled only to tyrosine residue 49 of EPO.

* * * * *